US009615768B2

(12) United States Patent
Nishihara et al.

(10) Patent No.: US 9,615,768 B2
(45) Date of Patent: Apr. 11, 2017

(54) MAGNETIC RESONANCE IMAGING APPARATUS AND IRRADIATION FREQUENCY ADJUSTING METHOD

(75) Inventors: Takashi Nishihara, Tokyo (JP); Hiroyuki Itagaki, Tokyo (JP); Tomohiro Goto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1417 days.

(21) Appl. No.: 13/496,916

(22) PCT Filed: Sep. 16, 2010

(86) PCT No.: PCT/JP2010/066046
§ 371 (c)(1),
(2), (4) Date: Mar. 19, 2012

(87) PCT Pub. No.: WO2011/037064
PCT Pub. Date: Mar. 31, 2011

(65) Prior Publication Data
US 2012/0176132 A1   Jul. 12, 2012

(30) Foreign Application Priority Data
Sep. 25, 2009   (JP) .................................. 2009-221292

(51) Int. Cl.
*G01R 33/48* (2006.01)
*A61B 5/055* (2006.01)
(Continued)

(52) U.S. Cl.
CPC .............. *A61B 5/055* (2013.01); *A61B 5/489* (2013.01); *G01R 33/446* (2013.01);
(Continued)

(58) Field of Classification Search
CPC .... A61B 5/055; A61B 5/489; G01R 33/4836; G01R 33/543; G01R 33/3875; G01R 33/243; G01R 33/446
(Continued)

(56) References Cited

U.S. PATENT DOCUMENTS

| 6,552,539 B2 | 4/2003 | Uetake |
| 2002/0145424 A1* | 10/2002 | Uetake ............. G01R 33/56563 |
| | | 324/307 |

(Continued)

FOREIGN PATENT DOCUMENTS

| JP | 4-26410 | 1/1992 |
| JP | 4-208133 | 7/1992 |

(Continued)

OTHER PUBLICATIONS

Translation of JP 2002-580.*
(Continued)

*Primary Examiner* — Melissa Koval
*Assistant Examiner* — Rishi Patel
(74) *Attorney, Agent, or Firm* — Cooper & Dunham LLP

(57) ABSTRACT

A high-quality image is obtained using a two-dimensional selective excitation method even if the static magnetic field is not uniform. Therefore, non-uniformity of a static magnetic field of a region to be focused in particular in a selective excitation region excited by 2DRF is measured, and a result of the measurement is reflected in an imaging sequence using the 2DRF. For example, a resonance frequency of magnetization obtained from the measurement result is set as an irradiation frequency of the 2DRF. In addition, a shim gradient magnetic field is applied so as to correct the non-uniformity of the magnetization obtained from the measurement result. These are applied only in the imaging sequence using the 2DRF, and an irradiation fre-
(Continued)

quency and a shim gradient magnetic field set in a conventional method are used in other imaging sequences.

15 Claims, 19 Drawing Sheets

(51) Int. Cl.
    *A61B 5/00*     (2006.01)
    *G01R 33/44*     (2006.01)
    *G01R 33/483*     (2006.01)
    *G01R 33/24*     (2006.01)
    *G01R 33/3875*     (2006.01)

(52) U.S. Cl.
    CPC ........ *G01R 33/4836* (2013.01); *G01R 33/243* (2013.01); *G01R 33/3875* (2013.01)

(58) Field of Classification Search
    USPC ........ 324/307, 309, 318, 321, 322; 382/131, 382/132; 600/410, 413, 419
    See application file for complete search history.

(56) References Cited

U.S. PATENT DOCUMENTS

2006/0255802 A1* 11/2006 Hirata .................... A61B 5/055
    324/318

2007/0279060 A1* 12/2007 Dannels ........... G01R 33/56563
    324/320

FOREIGN PATENT DOCUMENTS

| | | |
|---|---|---|
| JP | 11-216124 | 8/1999 |
| JP | 11-225987 | 8/1999 |
| JP | 2002-580 | 1/2002 |
| JP | 2002-291718 | 10/2002 |

OTHER PUBLICATIONS

Translation of JP11-216124.*
English translation of JP 2002000580 provided by Espacenet. Translation obtained Feb. 1, 2017.*
English translation of JP 11216124 provided by Espacenet. Translation obtained Feb. 1, 2017.*
International Search Report in PCT/JP2010/066046.
Mar. 4, 2015 Japanese official action in corresponding Japanese patent application No. 2011-532979.
John Pauly et al., "A k-Space Analysis of Small-Tip-Angle Excitation", Journal of Magnetic Resonance 81, 1989, pp. 43-56.
Yi Wang et al., "Navigator-Echo-based Real-Time Respiratory Gating and Triggering for Reduction of Respiration Effects in Three-dimensional Coronary MR Angiography", Cardiac Radiology, 1996, vol. 198, pp. 55-60.

* cited by examiner (a)

(b)

(a)

(b)

MAGNETIC RESONANCE IMAGING APPARATUS AND IRRADIATION FREQUENCY ADJUSTING METHOD

TECHNICAL FIELD

The present invention relates to a magnetic resonance imaging (hereinafter, referred to as "MRI") technique and in particular, to an imaging technique based on two-dimensional selective excitation in which a region restricted in an arbitrary two-dimensional direction is selectively excited.

BACKGROUND ART

Generally, in MRIs, only a one-dimensional direction is specified and an arbitrary plane with a predetermined thickness is selectively excited using a radio wave (hereinafter, referred to as an RF) and a gradient magnetic field. In addition, there is a spectral-spatial (hereinafter, referred to as SS) method of specifying two directions instead of the entire plane and exciting selectively only the inside of a region limited by the two directions (for example, refer to NPL 1). In the SS method, in order to realize such excitation, an RF for calculating a waveform from the excitation profile (hereinafter, referred to as a 2DRF) is applied together with an oscillating gradient magnetic field.

Since a signal can be acquired by exciting only the inside of a region selected by restriction in the two-dimensional direction in the SS method, a signal from the outside of the region can be effectively suppressed. For example, this SS method is used for the navigator echo sequence (hereinafter, referred to as navi-echo) for tracking the movement of the diaphragm (for example, refer to NPL 2). In the navi-echo, the vicinity of the diaphragm is excited in a cylindrical shape in a body axial direction using the SS method, and a temporal change of the diaphragm position in an axial direction of a region excited in the cylindrical shape is detected from signals generated from the region to monitor the respiratory motion.

CITATION LIST

Non Patent Literature

[NPL 1] A K-Space Analysis of Small-Tip-Angle Excitation, J. Pauly, D. Nishimura, J. Magn. Reson., 81, 43-56 (1989)
[NPL 2] Navigator-Echo-based Real-Time Respiratory Gating and Triggering for Reduction of Respiration Effects in Three-dimensional Coronary MR Angiography, Yi Wang, et al, Radiology, 198, 55-60 (1996)

SUMMARY OF INVENTION

Problems to be Solved

In MRIs, an irradiation frequency of an RF used for main imaging is usually determined on the basis of a resonance frequency of nuclear magnetization obtained from signals collected by a scan performed before the main imaging (hereinafter, referred to as a prescan). In this prescan, signals are collected from the entire imaging region of the main imaging.

In the imaging region, there is a dispersion (about tens of Hertz to 100 [Hz]) of the resonance frequency due to non-uniformity of a static magnetic field. Accordingly, when the irradiation frequency of the RF is determined on the basis of the resonance frequency obtained by the prescan, a deviation of about tens of Hertz to 100 [Hz] occurs locally between the set irradiation frequency and the resonance frequency due to this dispersion. Hereinafter, this deviation is expressed as a difference $\Delta F$.

The influence of the difference $\Delta F$ of about tens of Hertz to 100 [Hz] on the excitation profile is very different between the one-dimensional slice selection excitation and the SS method. For example, in the one-dimensional slice selection excitation, when there is a difference $\Delta F$ of 50 [Hz] at the small slice selection gradient magnetic field strength Gs of 1 [mT/m], the slice position is shifted by about 1 [mm]. This shift amount is about 1 pixel of an image and has almost no effect on the image.

In the 2DRF used in the SS method, however, the obtained excitation profile deforms from the desired shape if there is a difference $\Delta F$ between the set irradiation frequency and the resonance frequency. Generally, as the diameter (hereinafter, referred to as $\phi$) of the excitation profile increases, a flip angle (hereinafter, referred to as an FA) becomes small in proportion to the increase. For example, assuming that FA and $\phi$ of the desired excitation profile are 90 [deg] and 30 [mm], FA and $\phi$ of the obtained excitation profile are about 80 [deg] (89%) and about 37 [mm] when Duration (irradiation time) of the RF is 8 [ms] and there is a difference $\Delta F$ of 50 [Hz] at the slice selection gradient magnetic field strength Gs of 1 [mT/m].

In the SS method, if the excitation profile of the 2DRF deforms, a place which should not be excited originally is excited. As a result, the acquired image deteriorates. In particular, when the 2DRF is used as an excitation pulse of main imaging or as a pulse applied before the main imaging (hereinafter, referred to as a prepulse), the influence on an image obtained eventually is large.

The present invention has been made in view of the above-described situation, and it is an object of the present invention to provide a technique capable of obtaining a high-quality image using a two-dimensional selective excitation method even if the static magnetic field is not uniform.

Means for Solving the Problems

In the present invention, non-uniformity of a static magnetic field of a region to be focused in particular in a selective excitation region excited by 2DRF is measured, and a result of the measurement is reflected in an imaging sequence using the 2DRF. For example, a resonance frequency of magnetization obtained from the measurement result is set as an irradiation frequency of the 2DRF. In addition, a shim gradient magnetic field is applied so as to correct the non-uniformity of the magnetization obtained from the measurement result. These are applied only in the imaging sequence using the 2DRF, and an irradiation frequency and a shim gradient magnetic field set in a conventional method are used in other imaging sequences.

Specifically, there is provided a magnetic resonance imaging apparatus for collecting echo signals generated by applying a high-frequency magnetic field and a gradient magnetic field to an object placed in a static magnetic field according to a predetermined pulse sequence and reconstructing an image from the echo signals. The magnetic resonance imaging apparatus is characterized in that it includes: an irradiation frequency adjustment means that reduces a difference between a selective excitation irradiation frequency, which is an irradiation frequency of a high-frequency magnetic field when executing a two-dimensional selective excitation type pulse sequence, and a resonance frequency of magnetization within a focus region in a region excited by the two-dimensional selective excitation type pulse sequence; and a control means that executes the two-dimensional selective excitation type pulse sequence using a result obtained in the irradiation frequency adjustment means.

In addition, there is provided an irradiation frequency adjusting method of adjusting an irradiation frequency when executing a two-dimensional selective excitation type pulse sequence in a magnetic resonance imaging apparatus. The irradiation frequency adjusting method is characterized in that it includes: a focus region setting step of setting a focus region in a region excited by the two-dimensional selective excitation type pulse sequence; a signal collection step of collecting echo signals from the focus region using an initial irradiation frequency set in advance; and a frequency setting step of calculating an irradiation frequency from the echo signals collected from the focus region and setting the calculated irradiation frequency as a selective excitation irradiation frequency which is an irradiation frequency of the two-dimensional selective excitation type pulse sequence.

Advantageous Effects of Invention

According to the present invention, even if the static magnetic field is not uniform, it is possible to obtain a high-quality image using a two-dimensional selective excitation method.

MODES FOR CARRYING OUT THE INVENTION

First Embodiment

Figure 1:
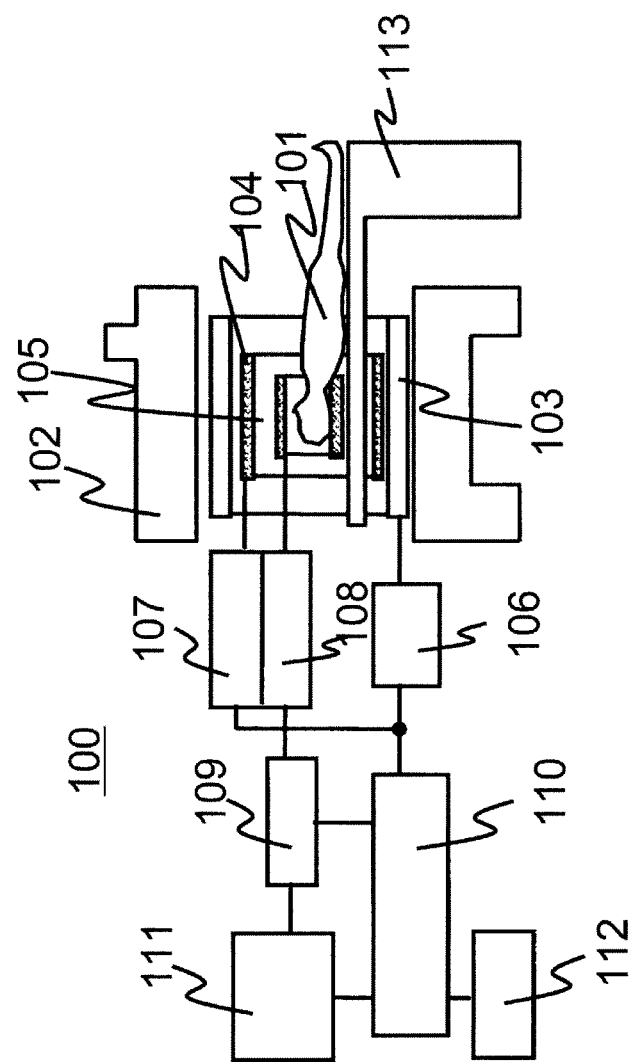
FIG. 1 is a functional block diagram of an MRI apparatus of a first embodiment.

Hereinafter, a first embodiment to which the present invention is applied will be described. Hereinafter, in all drawings for explaining the embodiments of the present invention, the same reference numerals are given to elements with the same functions, and repeated explanation thereof will be omitted.

First, the configuration of an MRI apparatus of the present embodiment will be described. FIG. 1 is a functional block diagram of an MRI apparatus 100 of the present embodiment. The MRI apparatus 100 of the present embodiment includes a magnet 102, a gradient magnetic field coil 103, a high-frequency magnetic field (RF) coil 104, an RF probe 105, a gradient magnetic field power source 106, an RF transmission unit 107, a signal detection unit 108, a signal processing unit 109, a control unit 110, a display unit 111, an operation unit 112, and a bed 113.

The magnet 102 generates a static magnetic field in a region (examination space) around an object 101. The gradient magnetic field coil 103 is formed by coils in three directions of X, Y, and Z directions, and generates a gradient magnetic field in an examination space according to a signal from the gradient magnetic field power source 106. The RF coil 104 applies (emits) an RF to the examination space according to the signal from the RF transmission unit 107. The RF probe 105 detects an MR signal generated by the object 101. The signal received by the RF probe 105 is detected by the signal detection unit 108, is subjected to signal processing by the signal processing unit 109, and is input to the control unit 110. The control unit 110 reconstructs an image from the input signal and displays it on the display unit 111.

In addition, the control unit 110 controls the operations of the gradient magnetic field power source 106, the RF transmission unit 107, and the signal detection unit 108 according to the time chart of control stored in advance and the imaging parameters input by the operator through the operation unit 112. In addition, the time chart of control is generally called a pulse sequence. The bed 113 is for an object lying thereon.

In addition, the MRI apparatus 100 may further include a shim coil for correcting the non-uniformity of the static magnetic field of the examination space and a shim power source for supplying a current to the shim coil.

Currently, a target to be imaged in MRI is a proton which is a main component of the object 101. The shapes or functions of the head, abdomen, limbs, and the like of the human body are imaged in a two-dimensional or three-dimensional manner by imaging the spatial distribution of proton density or the spatial distribution of relaxation of the excited proton.

Figure 2:
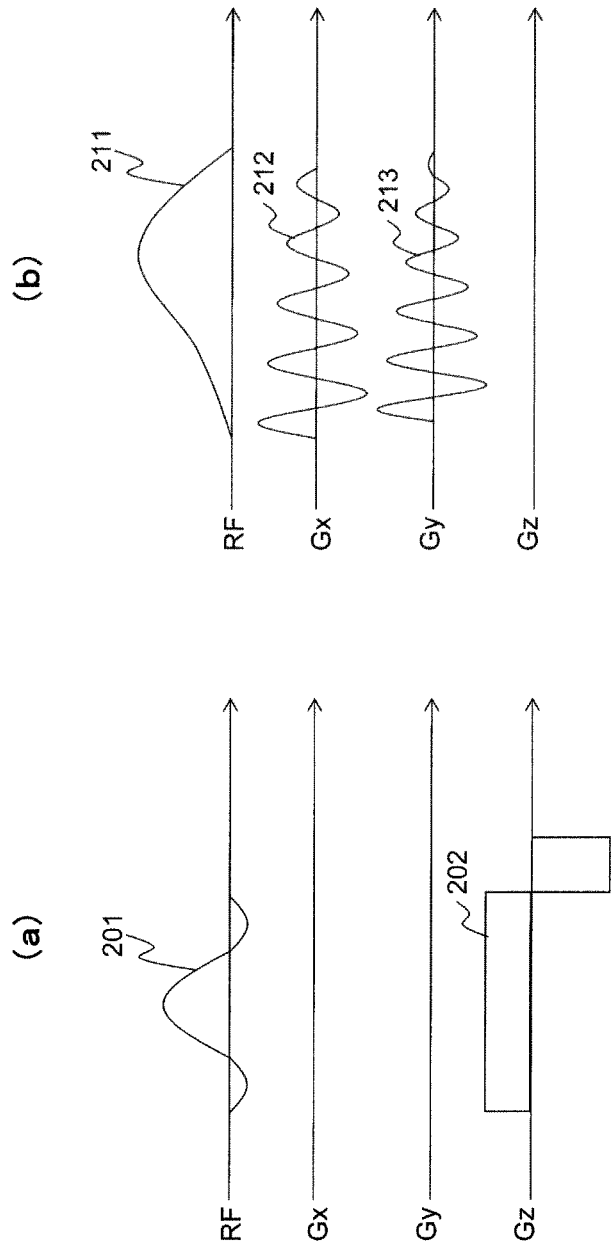
FIG. 2(a) is a pulse sequence diagram based on a conventional excitation method.
FIG. 2(b) is a pulse sequence diagram based on an SS method of the first embodiment.

In the present embodiment, an SS method of exciting a predetermined spatial region selectively is used for imaging. Here, a pulse sequence of the SS method will be described by comparing it with a pulse sequence in a conventional excitation method. FIG. 2 is a view for explaining the pulse sequence based on the SS method of the present embodiment by comparing it with a pulse sequence based on the conventional excitation method. FIG. 2(a) shows a pulse sequence based on the conventional excitation method, and FIG. 2(b) shows a pulse sequence based on the SS method used in the present embodiment.

As a conventional method, an example of exciting selectively an arbitrary slice for which only a position in the z-axis direction is specified is shown. In addition, in the SS method, an example is shown in which an arbitrary columnar region, for which only the shape on the xy plane is specified, is selectively excited. Here, the shape specified on the xy plane is assumed to be a circle. Moreover, in the pulse sequence diagram of this specification, RF, Gx, Gy, and Gz are timing charts of application of a high-frequency magnetic field (RF) pulse, a gradient magnetic field in an x-axis direction, a gradient magnetic field in a y-axis direction, and a gradient magnetic field in a Z direction, respectively.

As shown in FIG. 2(a), in the conventional method, a slice selection gradient magnetic field (Gz) 202 which is fixed in the z-axis direction is given at the time of application of an RF 201. Accordingly, a predetermined slice for which only a position in the z-axis direction is specified is selectively excited. On the other hand, in the SS method, an RF (2DRF) 211 is applied together with an oscillating gradient magnetic field (Gx) 212 in the x-axis direction and an oscillating gradient magnetic field (Gy) 213 in the y-axis direction, as shown in FIG. 2(b). Accordingly, a cylindrical region with an axis parallel to the z axis is selectively excited. In any method, phase encoding is applied to echo signals obtained from the excited region, and the echo signals are sampled in time series and are disposed in a k space.

An image is obtained by performing a Fourier transform on the echo signals (data) disposed in the k space. Here, as the number of phase encoding, the value of 128, 256, 512, or the like per image is usually selected. In addition, the value of 128, 256, 512, or 1024 is selected as the sampling number.

Generally, there is a region, which is to be focused in particular, in a region excited by the 2DRF. In the present embodiment, echo signals are actually collected from the region to be focused in the region excited by the 2DRF, and the optimal irradiation frequency of the region is determined using the result. Then, the 2DRF is irradiated using the determined irradiation frequency. Hereinafter, this processing is called irradiation frequency adjustment processing. In addition, an irradiation frequency determined in the conventional method, that is, an irradiation frequency determined on the basis of echo signals obtained from the entire imaging region is used as the irradiation frequency of RF applied at the time of echo signal collection in irradiation frequency adjustment processing. Hereinafter, the configuration of the MRI apparatus 100 of the present embodiment which realizes this and the procedure of processing will be described.

Figure 3:
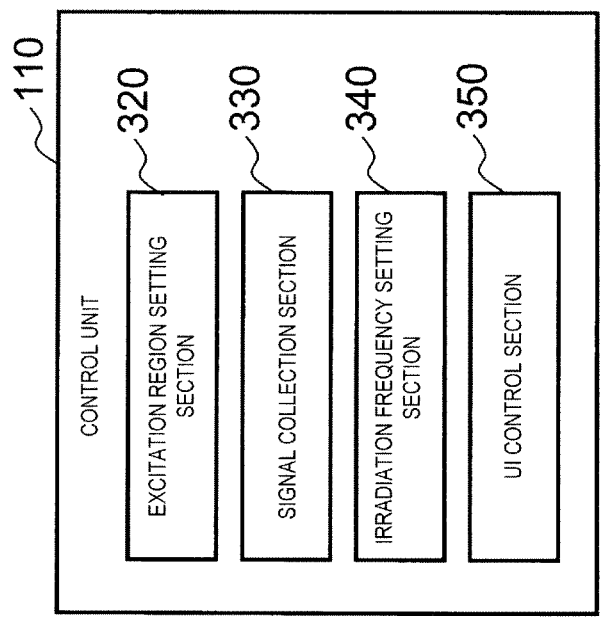
FIG. 3 is a functional block diagram of a control unit of the first embodiment.

FIG. 3 is a functional block diagram of the control unit 110 of the MRI apparatus 100 of the present embodiment. The MRI apparatus 100 of the present embodiment realizes the above-described irradiation frequency adjustment processing using the control unit 110. In order to perform the irradiation frequency adjustment processing, the control unit 110 includes an excitation region setting section 320, a signal collection section 330, an irradiation frequency setting section 340, and a UI control section 350, as shown in FIG. 3.

The control unit 110 of the present embodiment includes a CPU, a memory, and a storage device, and each of the functions described above is realized when the CPU loads a program stored in the storage device to the memory and executes it.

Figure 4:
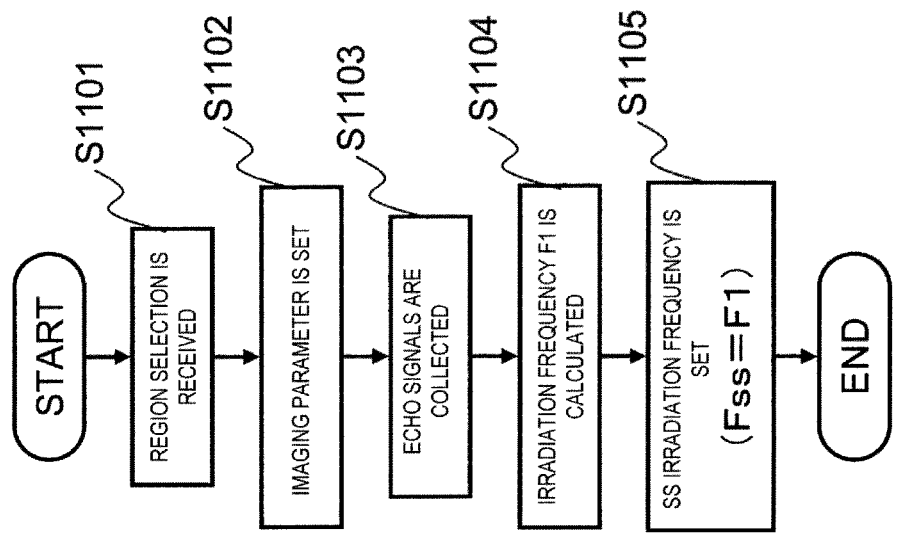
FIG. 4 is a flowchart of irradiation frequency adjustment processing of the first embodiment.

FIG. 4 is a processing flow of irradiation frequency adjustment processing of the 2DRF of the present embodiment. Moreover, in advance of this irradiation frequency adjustment processing, the overall irradiation frequency F0 is determined from signals of the entire imaging region in the conventional method.

The UI control section 350 displays a UI screen on the display unit 111 and receives the input of a two-dimensional selection region excited by the 2DRF and a local selection region, which is a region to be focused in particular of the two-dimensional selection region (step S1101). When the input of the two-dimensional selection region and the local selection region is received through the UI screen, the UI control section 350 notifies the excitation region setting section 320 of the corresponding region.

The excitation region setting section 320 sets an imaging parameter so as to excite the received local selection region according to the imaging sequence set in advance (step S1102). In this case, the overall irradiation frequency F0 is used as the irradiation frequency of the RF.

The signal collection section 330 executes the above-described imaging sequence with the imaging parameter set in step S1102, thereby obtaining echo signals from the local selection region (step S1103). Then, the irradiation frequency setting section 340 calculates an irradiation frequency F1 on the basis of the echo signals from the local selection region (step S1104), and sets the calculated irradiation frequency F1 as an irradiation frequency (SS irradiation frequency) Fss of the RF (2DRF) used in the SS method (step S1105). Details of the processing of steps S1103 and S1104 will be described later.

Through the above procedure, the SS irradiation frequency Fss is determined, and imaging based on the SS method is performed. For example, when using the SS method for main imaging, the control unit 110 performs imaging by setting the SS irradiation frequency Fss as the irradiation frequency of the RF in the main imaging. In addition, when using the SS method for prescan and performing the main imaging thereafter, the control unit 110 performs imaging using the SS irradiation frequency Fss at the time of prescan and using the overall irradiation frequency F0 in the main imaging.

Figure 5:
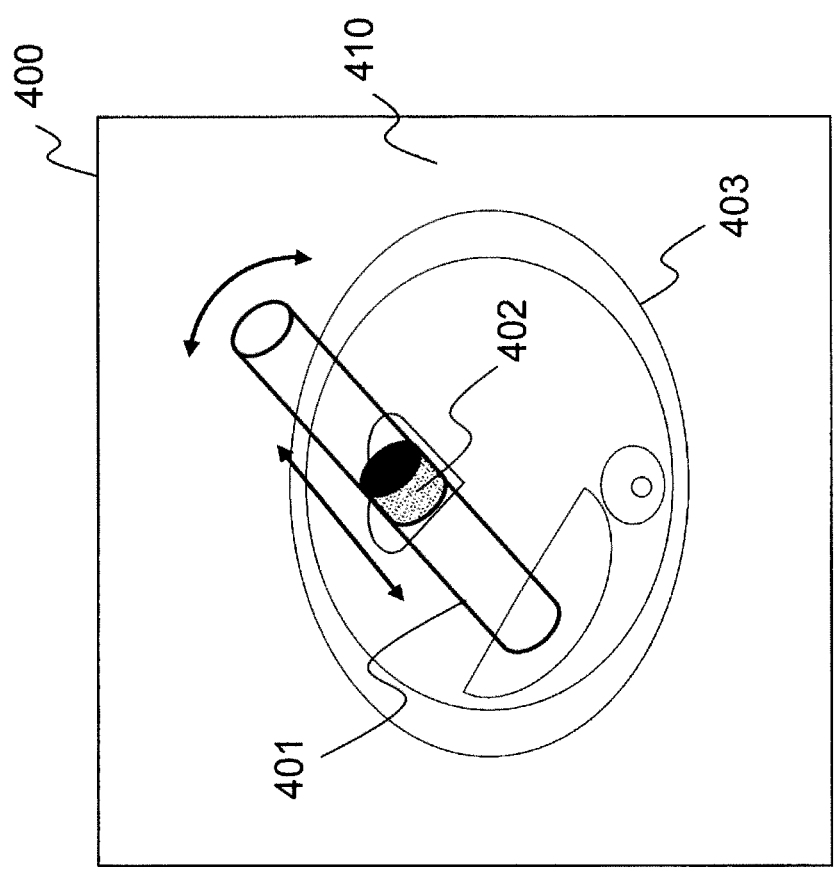
FIG. 5 is an explanatory view of a UI screen of the first embodiment.

Here, details of the setting of the two-dimensional selection region and the local selection region by the operator in the above step S1101 will be described. FIG. 5 is an example of a UI screen 400, which is generated by the UI control section 350 and displayed on the display unit 111, when selecting these regions.

As shown in this drawing, a positioning image 410 acquired in advance is displayed on the UI screen 400. On this positioning image 410, the operator sets a two-dimensional excitation selection region 401 and a local selection region 402. Here, the two-dimensional excitation selection region 401 is a cylindrical region excited by the SS method as described above here, and the local selection region 402 is a region to be focused in particular of the two-dimensional excitation selection region. Here, as an example, the local selection region 402 is made to have a cylindrical shape with the same axis as the two-dimensional excitation selection region 401 and the same radius of the cross section.

In addition, any input of the two-dimensional excitation selection region 401 and the local selection region 402 may be received first. For example, in the case of receiving the two-dimensional excitation selection region 401 first, the two-dimensional excitation selection region 401 may be set by arbitrary position and angle as indicated by the arrows in the drawing. Then, the local selection region 402 may slide in the axial direction of a cylinder within a region along the cylinder set as the two-dimensional excitation selection region 401 as indicated by the arrow in the drawing. In the case of receiving the local selection region 402 first, the two-dimensional excitation selection region 401 is received as a cylinder with the same axis as the set local selection region 402.

In FIG. 5, both the two-dimensional excitation selection region 401 and the local selection region 402 are formed as cylinders (columnar shapes), and their sectional shapes are circles. However, the two-dimensional excitation selection region 401 and the local selection region 402 are not limited to having these shapes. These sectional shapes may be set arbitrarily.

Figure 6:
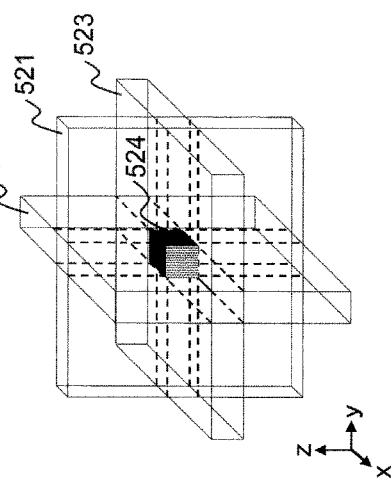
FIG. 6(a) is an explanatory view of a region excited by an orthogonal three cross-section excitation method of the first embodiment.
FIG. 6(b) is a pulse sequence diagram of the same orthogonal cross-section excitation method.
Figure 6:
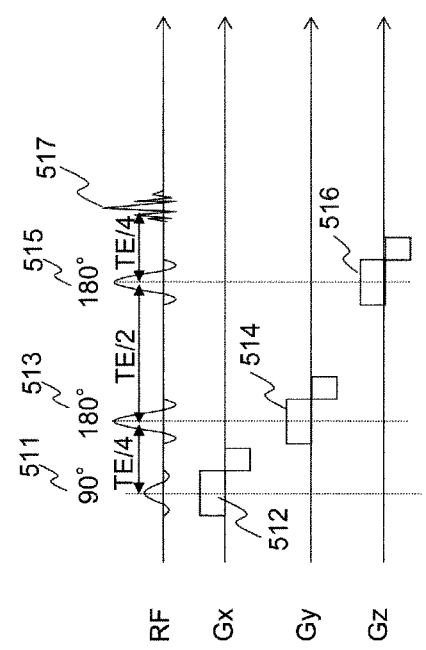

Next, details of the processing of steps S1103 and S1104 will be described. In the present embodiment, an orthogonal three cross-section excitation method is used as an imaging sequence for collecting signals from the local selection region 402. First, the imaging sequence based on this orthogonal three cross-section excitation method will be described. FIG. 6(a) is a view for explaining a region excited by orthogonal three cross-section excitation. In addition, FIG. 6(b) is a pulse sequence diagram of the orthogonal three cross-section excitation method. In addition, in FIG. 6(a), each cross section is transparently shown for the sake of explanation.

In the orthogonal three cross-section excitation method, a region (intersection region) 524 of a rectangular parallelepiped in which three perpendicular cross sections cross each other is excited. Here, the intersection region 524 is excited so that the cylindrical local selection region 402 is inscribed. In order to excite such a region, as shown in FIG. 6(b), a first gradient magnetic field 512 is applied in the x-axis direction (Gx) together with a 90° pulse 511, and a predetermined cross section (first cross section) 521 is excited in the x-axis direction. After echo time (TE)/4 from the application of the 90° pulse 511, a second gradient magnetic field 514 is applied in the y-axis direction (Gy) together with a first 180° pulse 513, and nuclear magnetization of a region where the first cross section 521 and a cross section (second cross section) 522 in the y-axis direction specified by this cross each other is excited. After time TE/2 from the application of a first 180° pulse 513, a third gradient magnetic field 516 is applied in the z-axis direction (Gz) together with a second 180° pulse 515, and nuclear magnetization of a region 524 where the first and second cross sections 521 and 522 and a cross section (third cross section) 523 in the z-axis direction specified by this cross each other is excited. Then, an echo signal 517 generated at the timing of time TE/4 after the application of the second 180° pulse 515 is collected. Moreover, in the imaging sequence described above, the order of application axes for the application of gradient magnetic fields does not matter.

The signal collection section 330 executes the above-described orthogonal cross-section excitation method to collect echo signals without encoding. Then, a Fourier transform of the collected signals is performed in a time direction. As a result of the Fourier transform, a histogram of a resonance frequency in the local selection region 402 is obtained.

The irradiation frequency setting section 340 scans the obtained histogram and specifies the center frequency in a band of ±several tens of Hertz from the maximum peak. Then, the frequency is calculated as the irradiation frequency and is set as the SS irradiation frequency Fss. In addition, a frequency at which the maximum peak is obtained may be set as the SS irradiation frequency Fss. In addition, the center of the entire band of the histogram may also be set as the SS irradiation frequency Fss.

As described above, according to the present embodiment, the irradiation frequency used as the 2DRF is determined using echo signals obtained from a region approximately matching a region which is actually excited by the 2DRF. Therefore, since the irradiation frequency used for the 2DRF approximately matches a resonance frequency of nuclear magnetization in the corresponding region, it is possible to suppress the deformation of an excitation profile of the 2DRF caused by the difference ΔF between both the frequencies.

That is, according to the present embodiment, even if the static magnetic field is not uniform, selective excitation can be performed by an RF having a desired excitation profile. As a result, since a desired region can be excited with high accuracy, the purpose of the selective excitation can be achieved with high accuracy. Therefore, a high-quality image can be obtained.

Moreover, in the above embodiment, the case where the orthogonal three cross-section excitation method is used as an imaging sequence, in which the signal collection section 330 collects signals from the local selection region 402, in step S1103 has been described as an example. However, the imaging sequence is not limited to this. For example, two-dimensional selective excitation may also be used. An example using the two-dimensional selective excitation will be described below.

Figure 7:
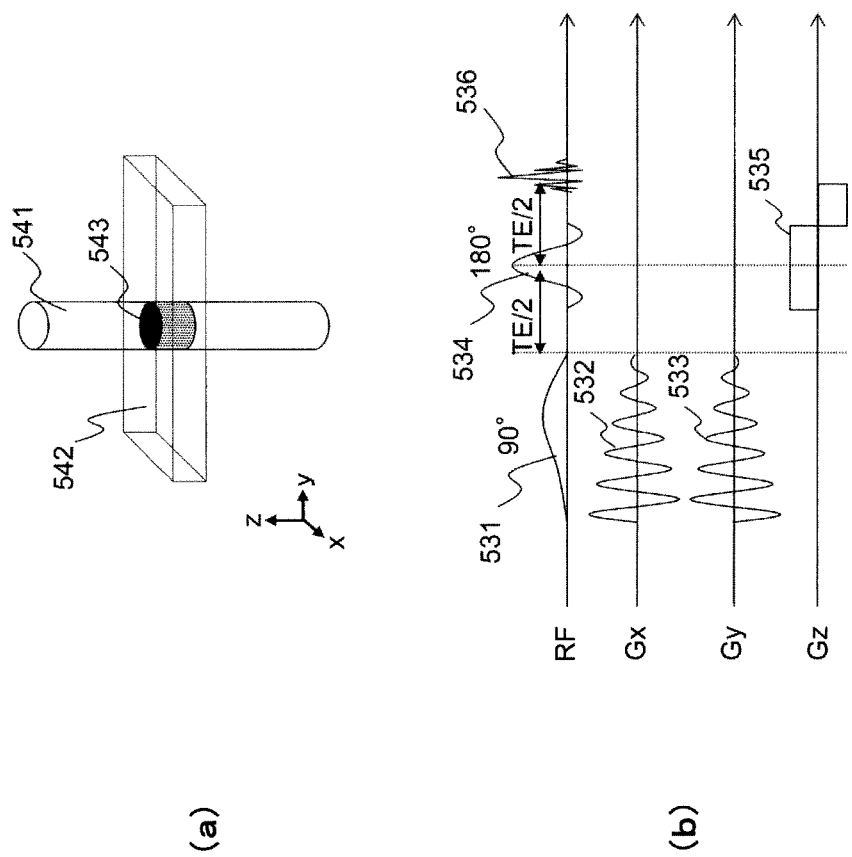
FIG. 7(a) is an explanatory view of a region excited by a 2D orthogonal 1D method of the first embodiment.
FIG. 7(b) is a pulse sequence diagram of the same 2D orthogonal 1D method.

FIG. 7 is a view for explaining an excitation region and an imaging sequence when two-dimensional selective excitation and excitation of one cross section, which is perpendicular to the axis of a cylindrical region excited by this two-dimensional selective excitation, are combined with each other (2D orthogonal 1D method). FIG. 7(a) is a view for explaining a region excited by the 2D orthogonal 1D method, and FIG. 7(b) is a pulse sequence diagram of the 2D orthogonal 1D method. In addition, in FIG. 7(a), each cross section and a cylindrical region are transparently shown for the sake of explanation.

In the 2D orthogonal 1D method, first, a first oscillating gradient magnetic field 532 is applied in the x-axis direction (Gx) and a second oscillating gradient magnetic field 533 is applied in the y-axis direction (Gy) together with the 90° pulse (2DRF) 531, so that the cylindrical region 541 is excited. After time TE/2 from the application of the 90° pulse (2DRF) 531, a gradient magnetic field 535 is applied in the Z-axis direction (Gz) together with a 180° pulse 534 so that the phase of nuclear magnetization of an intersection region 543 between a cross section 542 and the cylindrical region 541 is returned. Then, an echo signal 536 generated at the timing of time TE/2 after the application of the 180° pulse 534 is collected. Processing on the obtained echo signal and the method of calculating the SS irradiation frequency Fss are the same as in the embodiment described above.

Here, the imaging parameter is set such that the intersection region 543 matches the local selection region 402. In addition, the irradiation frequency used for the 90° pulse 531 of the imaging sequence described above is the overall irradiation frequency F0 determined in advance by the conventional method.

Figure 8:
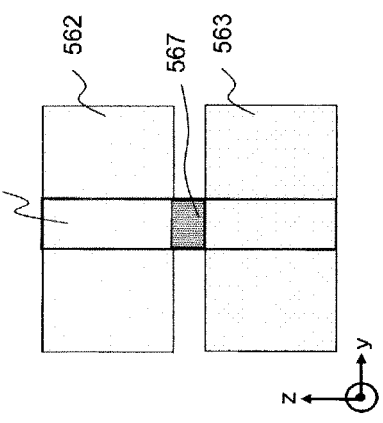
FIG. 8(a) is an explanatory view of a region excited by a 2D pre-saturation method of the first embodiment.
FIG. 8(b) is a pulse sequence diagram of the same 2D pre-saturation method.
Figure 8:
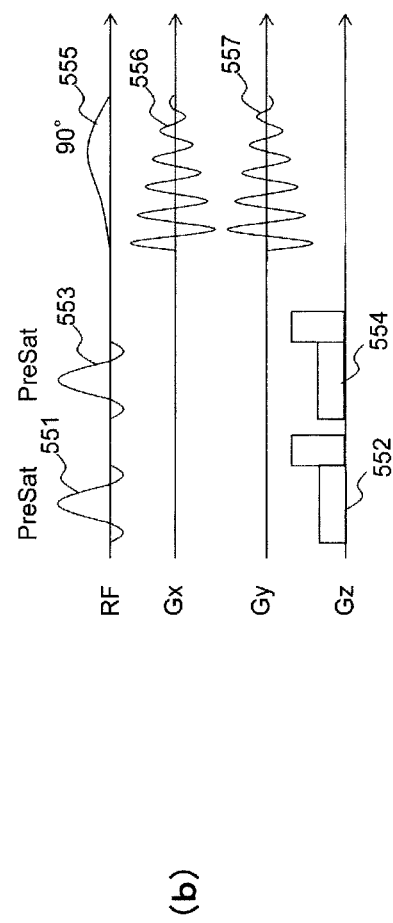

In addition, it is also possible to use two-dimensional excitation and an imaging sequence of suppressing echo signals from a region outside the local selection region 402 in the cylindrical region excited by this two-dimensional excitation (2D pre-saturation method). FIG. 8(a) is a view for explaining a region excited by the 2D pre-saturation method, and is a view seen from the x-axis direction. FIG. 8(b) is a pulse sequence diagram of the 2D pre-saturation method.

In the 2D pre-saturation method, first, a first gradient magnetic field 552 is applied in the z-axis direction (Gz) together with a first pre-saturation pulse 551 in order to demagnetize a first region 562. In addition, a second gradient magnetic field 554 is applied in the z-axis direction (Gz) together with a second pre-saturation pulse 553 in order to demagnetize a second region 563. Any of the first and second regions 562 and 563 may be magnetized first. Then, a first oscillating gradient magnetic field 556 is applied in the x-axis direction (Gx) and a second oscillating gradient magnetic field 557 is applied in the y-axis direction (Gy) together with the 90° pulse (2DRF) 555, so that a region (non-intersection region) 567 outside the first and second regions 562 and 563 in a cylindrical region 561 is excited. Then, an echo signal generated at the timing of time TE after the application of a 90° pulse (2DRF) 555 is collected. Processing on the obtained echo signal and the method of calculating the SS irradiation frequency Fss are the same as in the embodiment described above.

Here, the imaging parameter is set such that the non-intersection region 567 matches the local selection region 402. In addition, the irradiation frequency used for the 90° pulse 554 of the imaging sequence described above is the overall irradiation frequency F0 determined in advance by the conventional method.

In addition, when using the 2D orthogonal 1D method and the 2D pre-saturation method, an irradiation frequency registered in advance may be used instead of the overall irradiation frequency F0 obtained in advance by measurement. This is because the static magnetic field changes slightly when an object enters but the amount of change is small and accordingly, $\Delta F$ is almost the same even if the value obtained by multiplying the gyromagnetic ratio γ by the static magnetic field strength B0 is set as the overall irradiation frequency F0. In addition, the frequency used in the imaging sequence of the 2D orthogonal 1D method or the 2D pre-saturation method executed to calculate the SS irradiation frequency Fss is shifted by $\Delta F$ from the resonance frequency in the local selection region 402. Accordingly, the excitation profile of the 2DRF herein is different from a desired one. However, since the excited center position is the set position and the result of the resonance frequency does not change a lot, the obtained irradiation frequency F1 becomes a value near the actual resonance frequency in the local selection region 402 rather than the overall irradiation frequency F0.

Figure 9:
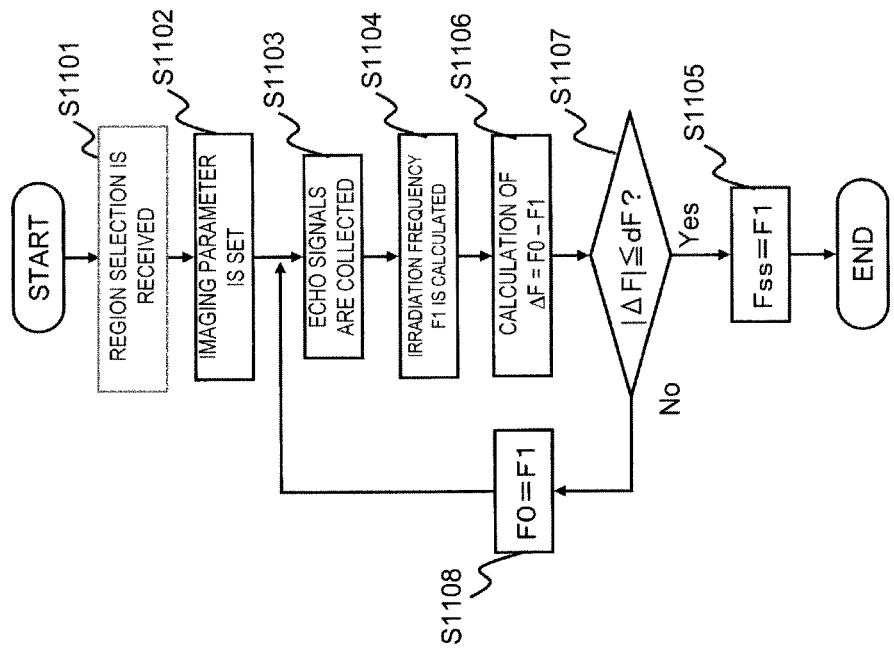
FIG. 9 is a flow chart of another example of the irradiation frequency adjustment processing of the first embodiment.

In addition, when using the 2D orthogonal 1D method and the 2D pre-saturation method for signal collection from the local selection region 402 in step S1103, feedback control may be performed. The flow of processing in this case is shown in FIG. 9. Processing up to step S1104 is the same as in FIG. 4.

After calculating the irradiation frequency F1 in step S1104, the irradiation frequency setting section 340 calculates the difference $\Delta F$ between F0 and F1 (step S1106). Then, it is determined whether or not the absolute value of the difference $\Delta F$ is equal to or less than the threshold value dF set in advance (step S1107). When the absolute value of the difference $\Delta F$ is larger than the threshold value dF, F1 is set as the irradiation frequency (F0=F1) of the 2DRF (step S1108), and the process returns to step S1103. Then, the signal collection section 330 collects echo signals from the local selection region 402, and the irradiation frequency F1' is calculated from the collected echo signals. This is repeated until the difference $\Delta F$ becomes equal to or less than the threshold value dF. When the difference $\Delta F$ becomes equal to or less than the threshold value dF, the calculated irradiation frequency F1 is set as the SS irradiation frequency Fss (step S1105).

Through such a configuration, an irradiation frequency can be set with higher accuracy than in the embodiment described above.

In addition, the threshold value dF is determined by the diameter φ of the excitation profile of the 2DRF requested for imaging and the flip angle FA of the excitation profile. The threshold value dF may be stored in advance in the storage device of the MRI apparatus 100 by the control unit 110 or may be determined and input by the operator. In addition, the irradiation frequency setting section 340 may calculate the threshold value dF from the accuracy of the diameter φ of the 2DRF and the flip angle FA set in advance by the operator.

Figure 10:
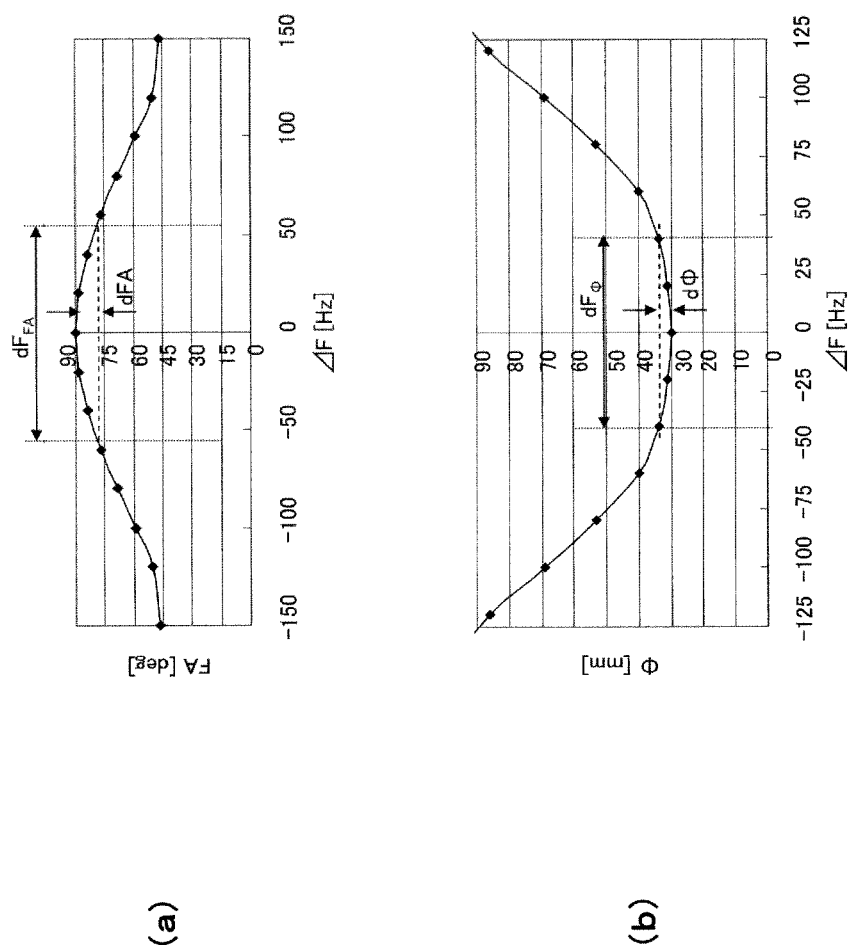
FIG. 10(a) is a graph showing the relationship between ΔF and FA of the first embodiment.
FIG. 10(b) is a graph showing the relationship between ΔF and φ of the first embodiment.

A method of calculating the dF by the irradiation frequency setting section 340 will be described. FIG. 10(a) is a graph showing the relationship between the difference $\Delta F$ and the flip angle FA, and FIG. 10(b) is a graph showing the relationship between the difference $\Delta F$ and the diameter φ. FIGS. 10(a) and 10(b) are graphs when Duration is 8 [ms], the diameter φ is 30 [mm], and the flip angle FA is 90 [deg]. In addition, the shapes of these graphs change depending on the waveform of 2DRF, Duration (irradiation time), and k space trajectory (shape of the oscillating gradient magnetic field).

In the graph of FIG. 10(a), the accuracy (allowable range) of the set flip angle FA is set to dFA, and a band $dF_{FA}$ equivalent to dFA is calculated from the maximum flip angle FA. Moreover, in the graph of FIG. 10(b), the accuracy (allowable range) of the set diameter φ is set to dφ, and a band $dF_φ$ equivalent to dφ is calculated from the minimum diameter φ. In addition, the smaller one of $dF_{FA}$ and $dF_φ$ is set as the threshold value dF.

In addition, the feedback control may be specified by the number of times. That is, a repeat count N (N is a natural number) is registered in advance. In addition, the processing of steps S1103, S1104, and S1107 in FIG. 9 by the signal collection section 330 and the irradiation frequency setting section 340 are performed N times which is the number of times set in advance.

Through such a configuration, the irradiation frequency of the 2DRF can be determined more accurately in the same manner as in the feedback control described above. In addition, since the number of times is set, the processing can be necessarily finished within a predetermined time.

In addition, the feedback control may also be performed in combination with a limit on the threshold value and a limit on the number of times. In this case, the irradiation frequency setting section 340 calculates ΔF whenever the irradiation frequency F1 is calculated once and determines whether or not the ΔF is equal to or less than the threshold value and whether or not the number of times of calculation of F1 amounts to N times of the number of times set in advance. When either of the cases is satisfied, the process ends.

Moreover, in this case, for example, when the number of times amounts to N times even though ΔF is not equal to or less than the threshold value, a warning indicating that the diameter ϕ and the flip angle FA of the excitation profile of the 2DRF have not reached predetermined accuracy may be displayed on the display unit 111. The irradiation frequency setting section 340 generates a warning from warning screen generating data stored in advance and displays it on the UI control section 350. In addition, in this state, a selection regarding whether or not to start imaging may be received. When an instruction to start imaging is received from the operator through the UI control section 350, the irradiation frequency setting section 340 sets (F0+ΔFmin), which is obtained by adding the minimum value ΔFmin of ΔF to F0, as the irradiation frequency Fss of the 2DRF. On the other hand, when an instruction not to start imaging is received, the feedback control is repeated.

Second Embodiment

Next, a second embodiment to which the present invention is applied will be described. The configuration of an MRI apparatus 100 of the present embodiment is basically the same as that in the first embodiment. However, irradiation frequency adjustment processing realized by the control unit 110 is different.

That is, in the first embodiment, signals from a region approximately matching the local selection region 402 are collected without encoding, and the SS irradiation frequency Fss is determined from a histogram obtained by a Fourier transform in the time direction. In the present embodiment, however, volume data of the region including the local selection region 402 is acquired, the static magnetic field distribution is acquired, and the SS irradiation frequency Fss is determined from the average value of the static magnetic field strength. Hereinafter, a different configuration from the first embodiment regarding the irradiation frequency adjustment processing by the control unit 110 of the present embodiment will be described. Other configurations and processing are the same as those in the first embodiment.

In the present embodiment, an imaging sequence capable of reconstructing a two-dimensional image is used as an imaging sequence for collecting signals from the local selection region 402. In this case, the overall irradiation frequency F0 is used as the irradiation frequency in the same manner as in the first embodiment. The excitation region setting section 320 sets an imaging parameter so as to excite a predetermined slice including the local selection region. In addition, the signal collection section 330 collects echo signals from the set slice including the local selection region 402. Then, a two-dimensional Fourier transform of the collected echo signals is performed to acquire the volume data of the region including the local selection region 402.

Figure 11:
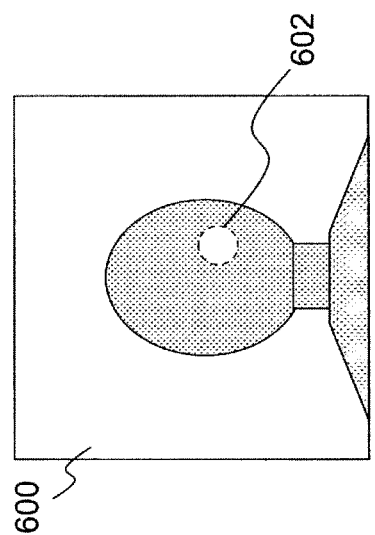
FIG. 11 is an explanatory view of a static magnetic field map of a second embodiment.

The volume data is a complex image. The irradiation frequency setting section 340 generates a static magnetic field map 600 shown in FIG. 11 using a phase component of this complex image. Then, in this static magnetic field map 600, the average value of the static magnetic field strength of a region 602 corresponding to the local selection region 402 is calculated, and the corresponding frequency F2 is set as Fss. In addition, it is preferable to select a region, which includes the local selection region 402 and which is perpendicular to the axis of the two-dimensional excitation selection region 401, as the region where the volume data is acquired.

Also in the present embodiment, the control unit 110 performs imaging based on 2DRF irradiation using the irradiation frequency Fss calculated through the above procedure, as in the first embodiment.

As described above, according to the present embodiment, it is possible to acquire the irradiation frequency Fss corresponding to the static magnetic field strength of the region excited by the 2DRF. Accordingly, since the irradiation frequency used for the 2DRF approximately matches a resonance frequency of nuclear magnetization in the corresponding region, it is possible to suppress the deformation of an excitation profile of the 2DRF caused by the difference ΔF between both the frequencies, as in the first embodiment.

In addition, according to the present embodiment, there is no influence of stimulated echo since RF irradiation is not performed 3 times or more in the irradiation frequency adjustment processing of the 2DRF. Therefore, the irradiation frequency can be determined more accurately. Moreover, since a prescan time is shortened in this case, it is possible to reconstruct an image with low spatial resolution by the acquired volume data.

In addition, it is also possible to use a result of shim imaging instead of the static magnetic field map. The shim imaging is an imaging for determining the value of a current flowing through a shim gradient magnetic field coil for eliminating the non-uniformity of the static magnetic field, and is performed before main imaging. A shim image obtained by shim imaging reflects the static magnetic field distribution, similar to the volume data described above. By using this shim imaging result, prescan performed to acquire the static magnetic field distribution becomes unnecessary. Accordingly, the total imaging time is shortened, thereby improving the efficiency. In addition, in this case, the MRI apparatus 100 includes a shim coil and a shim power source.

Third Embodiment

Next, a third embodiment to which the present invention is applied will be described. An MRI apparatus of the present embodiment has basically the same configuration as in the second embodiment. However, the MRI apparatus of the present embodiment includes a shim coil and a shim power source. In addition, in the second embodiment, the irradiation frequency Fss matching the resonance frequency of nuclear magnetization in the local selection region 402 is calculated on the basis of the obtained static magnetic field distribution (volume data and a shim image). In the present embodiment, however, a static magnetic field is adjusted so that the resonance frequency of nuclear magnetization of the corresponding region matches the overall irradiation frequency F0, which is acquired in advance, on the basis of these.

Figure 12:
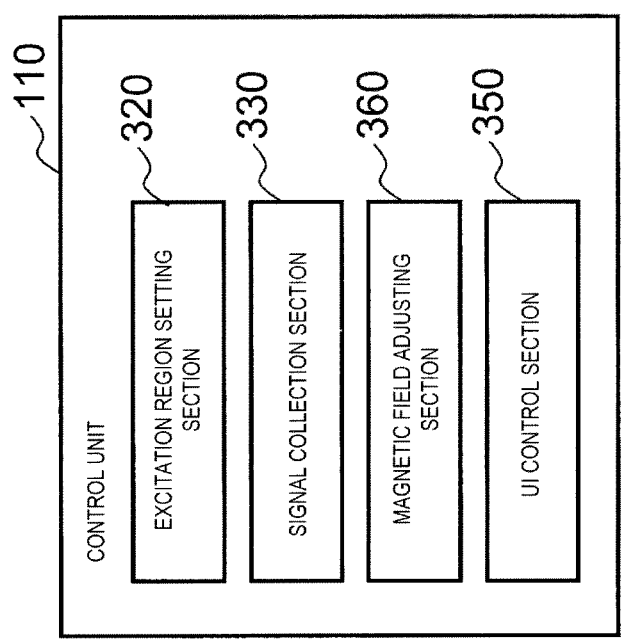
FIG. 12 is a functional block diagram of a control unit of a third embodiment.

FIG. 12 is a functional block diagram of the control unit 110 of the present embodiment. In the present embodiment, in order to realize the functions described above, a magnetic field adjusting section 360 which adjusts a magnetic field of a corresponding region is provided instead of the irradiation frequency setting section 340. Hereinafter, magnetic field adjustment processing of the magnetic field adjusting section 360 in the present embodiment, which is different from that in the second embodiment, will be described. Other configurations and processing are the same as those in the second embodiment.

The magnetic field adjusting section 360 of the present embodiment reduces the non-uniformity of the static magnetic field of a corresponding region in order to make the resonance frequency of nuclear magnetization in the local selection region 402 match the entire resonance frequency F0. Specifically, a shim current value Is for correcting the non-uniformity of the static magnetic field of the local selection region 402 is calculated from the volume data or the shim image, which is acquired by the signal collection section 330 using the same method as in the second embodiment, using the conventional method. In addition, the shim current is calculated only for the axis on which the current value can be changed during measurement (scan). In addition, the magnetic field adjusting section 360 controls the shim power source such that the value of a current applied to the shim coil in the axial direction is set as the calculated Is only during 2DRF application.

The magnetic field adjustment processing of the magnetic field adjusting section 360 will be described using FIGS. 13 and 14. In the magnetic field adjustment processing of the present embodiment, the shim current value Is for making the static magnetic field strength B1 in the local selection region 402 be the static magnetic field strength B0, which realizes the overall frequency F0, is calculated. Here, a case will be described in which the local selection region 402 has a cylindrical shape and the axial direction matches a z-axis direction of the examination space. In addition, it is assumed that a static magnetic field strength component can be corrected up to a first-order component at each axial direction of the shim coil. That is, a current value for making the overall irradiation frequency F0 match the resonance frequency F calculated from a zero-order component of the static magnetic field strength B1 is calculated.

Figure 13:
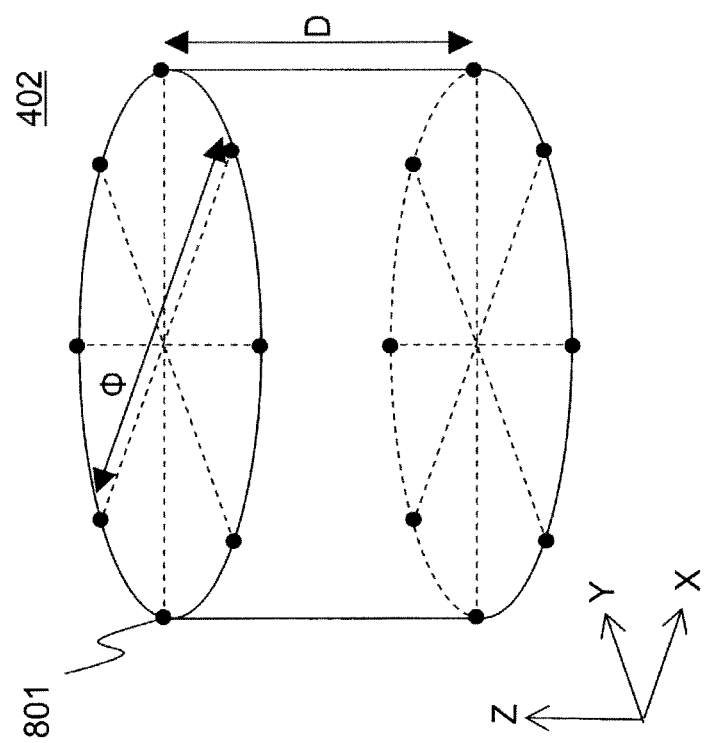
FIG. 13 is an explanatory view of an imaging result of a local selection region of the third embodiment.

FIG. 13 is an imaging result of the local selection region 402. Plural measurement points 801 are set on the circumference of the upper and lower surfaces of the cylindrical local selection region 402 with a diameter $\phi$ and a thickness D. In addition, it is preferable that the plural measurement points 801 be placed symmetrically with respect to the axis of this cylinder.

Figure 14:
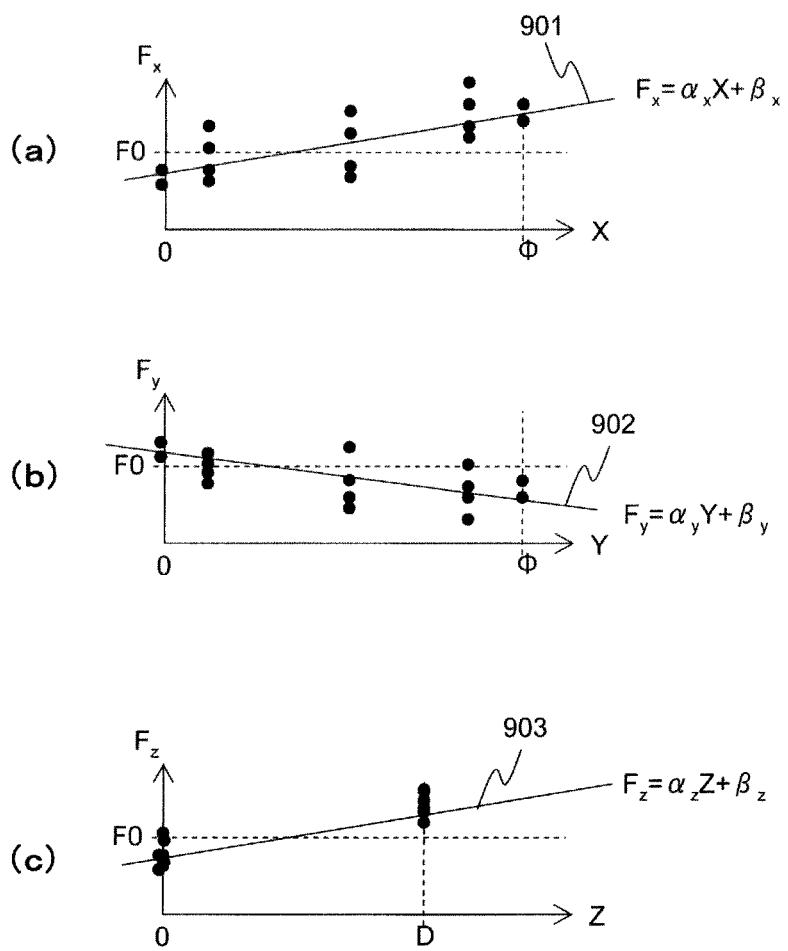
FIGS. 14(a) to 14(c) are explanatory views of a result of projection of the resonance frequency in each axial direction in the third embodiment.

A result obtained by projecting the resonance frequency F, which is calculated from the static magnetic field strength B1 of each measurement point 801, in each direction of the x, y, and z axes (Fx, Fy, Fz) and plotting it is shown in FIG. 14. In addition, FIG. 14($a$) is a result when the resonance frequency F is projected in the x-axis direction, FIG. 14($b$) is a result when the resonance frequency F is projected in the y-axis direction, and FIG. 14($c$) is a result when the resonance frequency F is projected in the z-axis direction. In each drawing, the horizontal axis is a position in each axial direction, and the vertical axis is the resonance frequency F calculated from the static magnetic field strength B1.

The projection result in each axial direction approximates the first-order equation. Here, it is assumed that the approximate equation 901 of the projection result in the x-axis direction is $F_x=\alpha_x x+\beta_x$, the approximate equation 902 of the projection result in the y-axis direction is $F_y=\alpha_y x+\beta_y$, and the approximate equation 903 of the projection result in the z-axis direction is $F_z=\alpha_z x+\beta_z$. The shim current value is determined such that all of them pass through F0 and their inclinations become 0. That is, the shim current value Is is a value which realizes the gradient magnetic field strength in which the approximate equations of an x-axis component, a y-axis component, and a z-axis component of the calculated resonance frequency F become $F'_x=-\alpha_x x-\beta_x+F0$, $F'_y=-\alpha_y x-\beta_y+F0$, and $F'_z=-\alpha_z x-\beta_z+F0$, respectively.

In the present embodiment, imaging is performed by applying the shim current value Is, which is calculated by the magnetic field adjusting section 360, only during 2DRF application in the method described above. Other than that, imaging is performed by applying the shim current value Is of or applying the shim current value which reduces the non-uniformity of the static magnetic field in the entire region to be imaged. As a result, according to the present embodiment, a desired excitation profile for the 2DRF can be acquired even if a static magnetic field is not uniform in the local selection region 402.

In addition, the correction order of non-uniformity of the static magnetic field using a shim coil is not limited to the above. A projection result of each measurement point 801 in each axial direction of the static magnetic field strength B1 can be made to approximate in a range of the order in which a shim coil in the corresponding axial direction can correct the static magnetic field strength. In addition, a method of calculating a shim current value for achieving the static magnetic field uniformity is not limited to the method described above. Various general methods may be used.

In addition, when the order in which non-uniformity of the static magnetic field can be corrected is a first order, it is possible to correct the non-uniformity of the static magnetic field using a gradient magnetic field based on the gradient magnetic field coil 103. That is, control is performed such that the same amount of current as the shim current value Is calculated by the above-described method is supplied from the gradient magnetic field power source 106 to each gradient magnetic field coil 103 as offset only during 2DRF application.

By correcting the non-uniformity of the static magnetic field using the gradient magnetic field coil 103, the non-uniformity of the static magnetic field of the local selection region 402 can be corrected during 2DRF application even if the MRI apparatus 100 does not include a shim coil. Therefore, since the 2DRF can be executed with an irradiation frequency without the difference ΔF, it is possible to suppress the deformation of an excitation profile of the 2DRF.

In addition, the irradiation gain of the RF and the gradient magnetic field strength may be adjusted using a difference ΔF1 remaining after correcting the non-uniformity of the static magnetic field by the shim magnetic field based on a shim coil or the gradient magnetic field based on a gradient magnetic field coil.

In this case, the magnetic field adjusting section 360 generates the static magnetic field map 600 from the volume data using the same method as in the second embodiment. Then, a magnetic field generated by the acquired shim current value Is or a current for gradient magnetic field correction (called a gradient magnetic field for correction) is added to the static magnetic field map 600. An absolute value lΔF1l of the difference ΔF1 (ΔF1=F3−F0) between a resonance frequency F3, which corresponds to the static magnetic field after correction using the gradient magnetic field for correction, and F0 is calculated. A flip angle FA1 and a diameter $\phi$1 corresponding to lΔF1l are read by referring to the graph showing the relationship between lΔF1l and the flip angle FA and the graph showing the relationship between lΔF1l and the diameter $\phi$. In addition, the graph showing the relationship between ΔF1 and the flip angle FA and the graph showing the relationship between ΔF1 and the diameter $\phi$ become graphs (ΔF is assumed to be ΔF1) shown in FIGS. 10(a) and 10(b) when Duration is 8 [ms], the diameter φ is 30 [mm], and the flip angle FA is 90 [deg].

Then, the magnetic field adjusting section 360 calculates the RF irradiation gain value such that the product of the irradiation gain of RF and the flip angle is fixed. That is, assuming that the RF gain before correction is RFGain0 and the flip angle before correction is FA0, RFGain1 after correction is obtained by the following Expression (1).

$$RFGain1 = FA0/FA1 \times RFGain0 \qquad (1)$$

In addition, the magnetic field adjusting section 360 calculates a gradient magnetic field strength value such that the ratio of the gradient magnetic field strength and the diameter is fixed. That is, assuming that the gradient magnetic field strength before correction is GC0 and the diameter before correction is φ0, the gradient magnetic field strength after correction GC1 is obtained by the following Expression (2).

$$GC1 = \phi1/\phi0 \times GC0 \qquad (2)$$

The control unit 110 performs control so as to execute the imaging sequence using the RF irradiation gain value RFGain1 and the gradient magnetic field strength GC1, which are acquired by the magnetic field adjusting section 360, at the time of 2DRF application. Accordingly, since the flip angle FA and the diameter φ of the 2DRF can be controlled more accurately, it is possible to come closer to the desired excitation profile.

Fourth Embodiment

Figure 15:
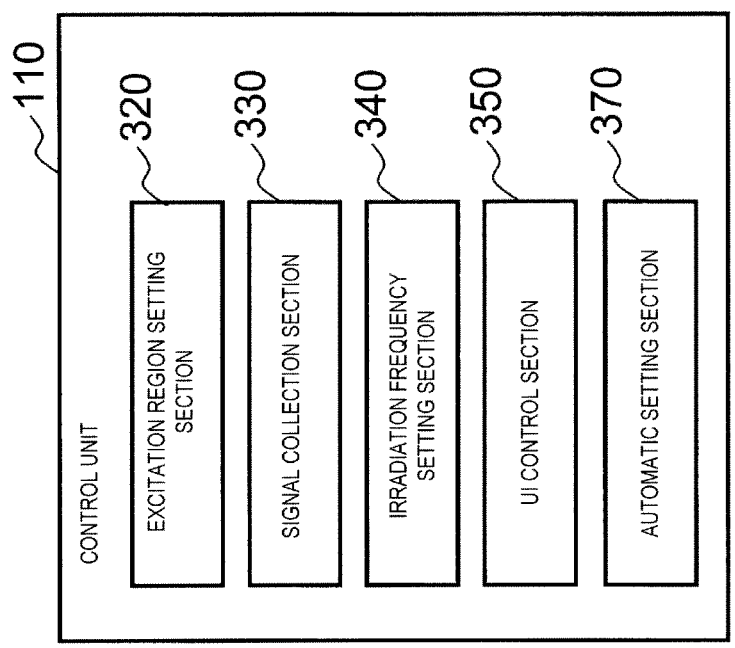
FIG. 15 is a functional block diagram of a control unit of a fourth embodiment.

Next, a fourth embodiment to which the present invention is applied will be described. In the present embodiment, the setting of a local selection region is further automated. For this reason, the control unit 110 of the present embodiment further includes an automatic setting section 370 for automatic setting of a local selection region in addition to the function of the control unit 110 according to anyone of the embodiments described above. FIG. 15 shows a functional block diagram of the control unit 110 of the present embodiment. Here, a functional block diagram based on the control unit 110 of the first embodiment is shown. In addition, other configurations of the MRI apparatus of the present embodiment are basically the same as those in each of the embodiments described above. The following explanation will be given focusing on a different configuration on the basis of the first embodiment.

Figure 16:
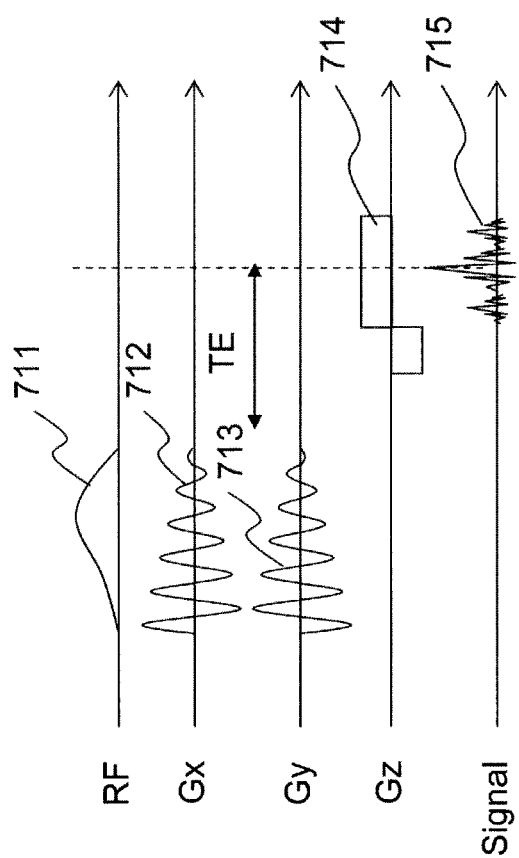
FIG. 16 is a sequence diagram of the imaging sequence of the fourth embodiment.
Figure 17:
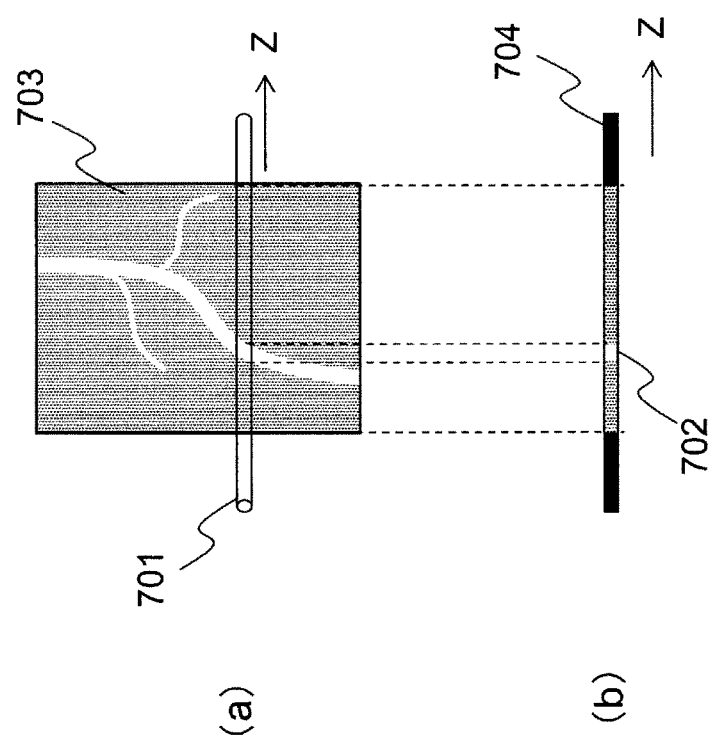
FIG. 17(a) is an explanatory view of a region where signals are collected with the imaging sequence shown in FIG. 16.
FIG. 17(b) is an explanatory view of a result obtained by a Fourier transform of signals collected by the same imaging sequence.

Here, a case where a target excited by the 2DRF is a portion having a water component, such as a blood vessel, as a main component will be described as an example. FIG. 16 is an example of an imaging sequence executed when the automatic setting section 370 specifies a local selection region. FIG. 17(a) shows a region 703 where echo signals are collected by the imaging sequence shown in FIG. 16. Here, 701 is a two-dimensional selection region. Moreover, here, it is assumed that the axial direction of the cylindrical two-dimensional selection region 701 is a z-axis.

In the imaging sequence shown in FIG. 16, a 2DRF 711 is applied as a frequency for exciting only a water signal together with oscillating gradient magnetic fields 712 and 713, so that only a band of water in the two-dimensional selection region 701 is excited. Then, after echo time (TE), echo signals 715 are collected while applying a read gradient magnetic field 714 in the Z-axis direction (Gz). Then, a Fourier transform of the collected echo signals 715 is performed.

A result 704 of the Fourier transform at this time is shown in FIG. 17(b). Thus, the result 704 becomes a projection image 704 of the two-dimensional selection region 701 in the Z-axis direction. It is known that the portion having a water component, such as a blood vessel, as a main component shows a high signal on a projection image. Therefore, a high-signal place 702 on this projection image 704 is the local selection region 402 in an intersection region of the two-dimensional selection region 701 and the blood vessel.

Using this, the automatic setting section 370 of the present embodiment scans the Fourier transform result 704 and determines that a region with a value equal to or greater than a threshold value set in advance is the local selection region 402. That is, when the two-dimensional selection region 401 is received through the UI screen 400, the automatic setting section 370 executes the above-described processing to specify the local selection region 402. In addition, irradiation frequency adjustment processing after the local selection region 402 is specified is the same as that in each of the embodiments described above.

As described above, according to the present embodiment, the setting of the local selection region is automated in the irradiation frequency adjustment processing. Therefore, in addition to the effect obtained by each of the embodiments described above, an effect that the operator's time and effort can be reduced is further obtained. In addition, since the local selection region is determined from the measurement result, the local selection region can be set with stable accuracy without depending on the skill of the operator.

Although the case where the automatic setting section 370 is added to the configuration of the first embodiment has been described as an example herein, the automatic setting section 370 may also be added to the configuration of any of the above embodiments.

Figure 18:
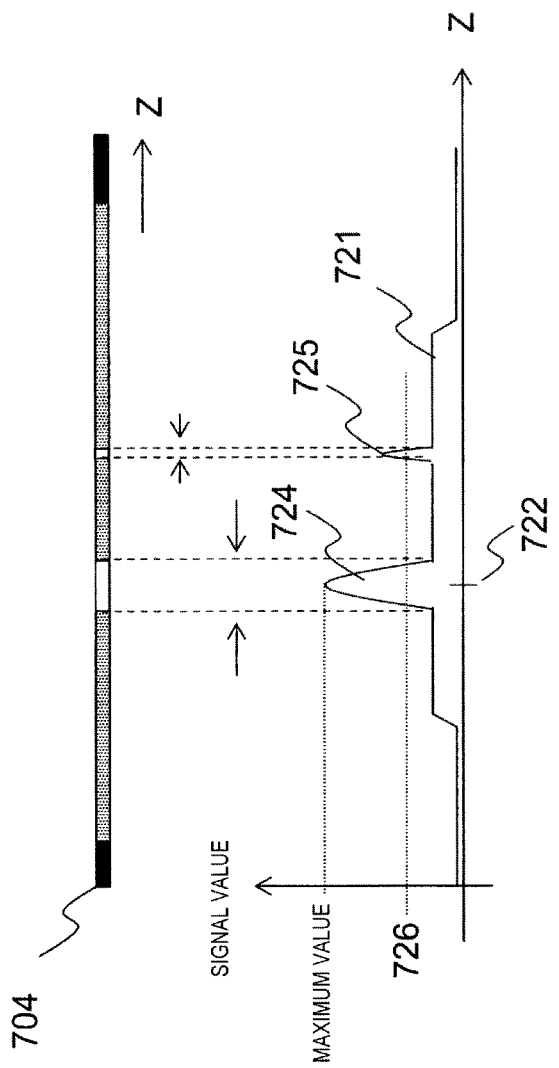
FIG. 18 is an explanatory view for describing a method of determining a local selection region of the fourth embodiment.

In addition, although the blood vessel position, that is, the local selection region 402 is specified as a position showing a signal equal to or greater than a threshold value in the embodiment described above, the specification method is not limited to this. For example, it may also be determined on a profile 721 of the projection image 704 shown in FIG. 18. For example, a position 722 showing the maximum signal strength on the profile 721 is specified as the center position of the local selection region 402. In this case, the width of the local selection region 402 in the z-axis direction is stored in advance in a storage device, and this is used. In addition, it is also possible to extract regions 724 and 725 showing the signal strength exceeding the threshold value 726 set in advance and to set a region with a maximum width among them as the local selection region 402. In addition, the center position of the region with a maximum width may be specified as the center position of the local selection region 402, and the width stored in advance in a storage device may be used as the width in the z-axis direction.

In addition, it is also possible to display the local selection region 402, which is determined from the projection image 704 by any of the methods described above, on the display unit 111 so that an adjustment from the operator can be received through the UI control section 350. Through such a configuration, a local selection region where the irradiation frequency is to be adjusted can be determined with higher accuracy.

In addition, in the imaging sequence shown in FIG. 16, a band including both water and fat may be set for the frequency of the 2DRF and TE may be set as "Out of Phase" by which a fat signal is suppressed, so that the echo signals 715 are collected at this timing. As a result, it is possible to obtain a projection image in which a signal from water is visualized as a high signal in the same manner as in the embodiment described above.

Generally, in the case of a band including both water and fat, duration of the RF can be shortened compared with that in the case of a band of only water. Therefore, through such a configuration, an imaging time for specifying the local selection region 402 can be shortened.

In addition, fat in a display may be visualized with a high signal according to the imaging condition. In this case, a projection image is generated after removing the signal from the fat of the epidermis, and the above-described processing is performed to specify the local selection region 402.

Figure 19:
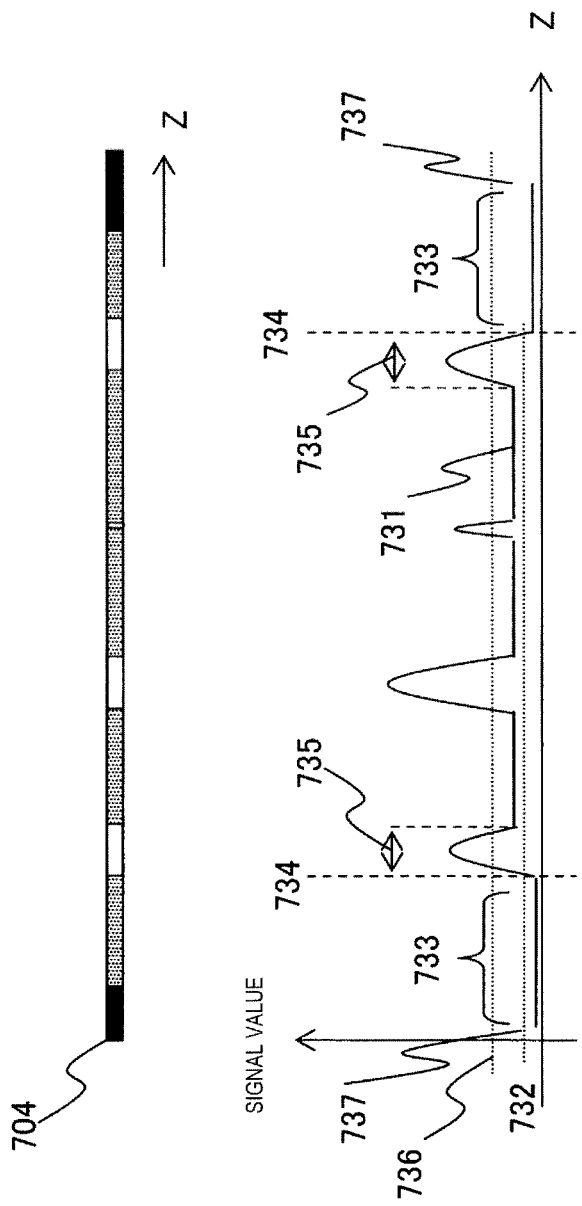
FIG. 19 is an explanatory view of another example for describing the method of determining a local selection region of the fourth embodiment.

Here, an example of the method of removing the signal from the fat of the epidermis will be described using FIG. 19. A profile 731 of the projection image 704 obtained by the method described above is scanned from both ends 737 toward the center, and a region 733 with a signal value equal to or less than a threshold value 732 set in advance is determined as a noise region. A region 735 having a width set in advance in an opposite direction to the end 737 from an edge portion 734 of the region 733, which is determined as a noise region, opposite the end 737 is determined as the fat of the epidermis. The signal of the determined region 735 is removed.

In addition, the width used to determine the region 735 may be stored in advance and may be determined on the profile 731. When the width is determined on the profile 731, for example, scanning is performed in an opposite direction to the end 737 from the edge portion 734, and a length until the signal value becomes equal to or less than a threshold value 736 set in advance is set as this width.

In addition, when a target of the local selection region 402 is a portion with a flow, such as a blood vessel, the local selection region 402 may be specified from the phase profile of the projection image 704. That is, the phase of the portion with a flow changes greatly due to this flow compared with other portions. By detecting this, it is possible to specify the blood vessel position, that is, the local selection region 402. Here, for example, a differential or a difference of the phase profile result is taken to detect the position to take its extreme value. Moreover, in this case, since the blood vessel position is visualized with a high signal, it is not influenced by fat.

As described above, according to each of the embodiments, it is possible to match the resonance frequency of nuclear magnetization to the irradiation frequency of the 2DRF in a focus region of the two-dimensional selective excitation region. Therefore, deviations of the diameter $\phi$ and the flip angle FA of the excitation profile of the 2DRF from those desired, which are caused by the non-uniformity of the static magnetic field, are reduced. That is, the excitation profile of the 2DRF is stabilized.

In addition, according to each of the embodiments described above, when the 2DRF is used for a prepulse, the irradiation frequency or the shim current value is changed in a prepulse sequence and main imaging. Accordingly, optimization of the excitation profile of the 2DRF can be realized without affecting the main imaging.

Therefore, according to the present embodiment, the excitation size (diameter $\phi$) and the flip angle FA of the 2DRF are stabilized even in the environment where the static magnetic field is not uniform. As a result, since the excitation profile is stabilized, a high-quality image can be obtained.

REFERENCE SIGNS LIST

100: MRI apparatus
101: object
102: magnet
103: gradient magnetic field coil
104: RF coil
105: RF probe
106: gradient magnetic field power source
107: RF transmission unit
108: signal detection unit
109: signal processing unit
110: control unit
111: display unit
112: operation unit
113: bed
201: RF
202: gradient magnetic field
211: RF
212: oscillating gradient magnetic field
213: oscillating gradient magnetic field
320: excitation region setting section
330: signal collection section
340: irradiation frequency setting section
350: UI control section
360: magnetic field adjusting section
370: automatic setting section
400: UI screen
401: two-dimensional selection region
402: local selection region
511: 90° pulse
512: first gradient magnetic field
513: first 180° pulse
514: second gradient magnetic field
515: second 180° pulse
516: third gradient magnetic field
517: echo signal
521: first cross section
522: second cross section
523: third cross section
524: intersection region
531: 90° pulse
532: first oscillating gradient magnetic field
533: second oscillating gradient magnetic field
534: 180° pulse
535: gradient magnetic field
536: echo signal
541: cylindrical region
542: cross section
543: intersection region
551: first pre-saturation pulse
552: first gradient magnetic field
553: second pre-saturation pulse
554: second gradient magnetic field
555: 90° pulse
556: first oscillating gradient magnetic field
557: second oscillating gradient magnetic field
561: cylindrical region
562: first region
563: second region
567: non-intersection region
600: static magnetic field map
701: two-dimensional selection region
702: place corresponding to local selection region
703: blood vessel
704: Fourier-transform result
711: 2DRF
712: oscillating gradient magnetic field
714: read gradient magnetic field
715: echo signal
722: maximum signal strength position 724: region
725: region
726: threshold value
731: profile
732: threshold values
733: region
734: edge portion
735: region
736: threshold value
737: both ends
737: end
801: measurement point
901: approximate equation
902: approximate equation
903: approximate equation

The invention claimed is:

1. A magnetic resonance imaging apparatus for collecting echo signals generated by applying a high-frequency magnetic field and a gradient magnetic field to an object placed in a static magnetic field according to a predetermined pulse sequence and reconstructing an image from the echo signals, comprising:
   an irradiation frequency adjustment unit to reduce a difference between a selective excitation irradiation frequency, which is an irradiation frequency of a two-dimensional selective excitation magnetic field when executing a two-dimensional selective excitation type pulse sequence, and a resonance frequency of magnetization within a focus region in a columnar region excited by the two-dimensional selective excitation magnetic field; and
   a control unit to execute the two-dimensional selective excitation type pulse sequence using a result obtained in the irradiation frequency adjustment unit.

2. The magnetic resonance imaging apparatus according to claim 1,
   wherein the irradiation frequency adjustment unit includes:
   a region setting section to set the focus region;
   a signal collection section to collect echo signals from the focus region using an initial irradiation frequency set in advance; and
   a frequency setting section to calculate an irradiation frequency from the echo signal when the signal collection section collects the echo signals and sets the calculated irradiation frequency as the selective excitation irradiation frequency.

3. The magnetic resonance imaging apparatus according to claim 2,
   wherein the initial irradiation frequency is calculated from a prescan result of an imaging region of main imaging.

4. The magnetic resonance imaging apparatus according to claim 2,
   wherein the frequency setting section calculates a frequency indicating a maximum peak on a histogram, which is obtained by performing a Fourier transform of the echo signals in a time direction, as the irradiation frequency.

5. The magnetic resonance imaging apparatus according to claim 2,
   wherein according to an orthogonal three cross-section excitation type pulse sequence in which a rectangular parallelepiped region including at least a part of the focus region is set as an intersection region, the signal collection section collects echo signals of the intersection region without encoding.

6. The magnetic resonance imaging apparatus according to claim 2, wherein the signal collection section collects echo signals of the focus region without encoding, according to a pulse sequence based on a combination of two-dimensional selective excitation of which the columnar region in which the focus region is inscribed is set as an excitation region and one-dimensional selective excitation of which the cross-section in which the focus region is inscribed and is orthogonal to the columnar region is set as an excitation region.

7. The magnetic resonance imaging apparatus according to claim 2, wherein the signal collection section collects echo signals of the focus region without encoding, according to a pulse sequence based on a combination of (i) a suppression pulse for suppressing a signal from a region other than a cross section which is perpendicular to the columnar region in which the focus region is inscribed, and (ii) two-dimensional selective excitation of which the columnar region in which the focus region is inscribed is set as an excitation region.

8. The magnetic resonance imaging apparatus according to claim 6,
   wherein the frequency setting section calculates an absolute value of a difference between the selective excitation irradiation frequency and the initial irradiation frequency after the irradiation frequency is calculated and compares the absolute value with a threshold value set in advance, and
   when a comparison result indicating that the absolute value is larger than the threshold value is obtained, the signal collection section collects echo signals from the focus region with the irradiation frequency as the initial irradiation frequency.

9. The magnetic resonance imaging apparatus according to claim 2,
   wherein the signal collection section acquires volume data from a region including the focus region, and
   the frequency setting section calculates an average value of static magnetic field distribution of the volume data and determines the irradiation frequency based on the calculated average value.

10. The magnetic resonance imaging apparatus according to claim 2, further comprising:
    a shim gradient magnetic field generation means that corrects non-uniformity of a static magnetic field of an imaging region,
    wherein the signal collection section acquires a shim image of a region including the focus region, and
    the frequency setting section calculates as the irradiation frequency an average value of static magnetic field distribution obtained by the shim image.

11. The magnetic resonance imaging apparatus according to claim 2,
    wherein the irradiation frequency adjustment unit sets the initial irradiation frequency for a two-dimensional selective excitation magnetic field of a pulse sequence other than the two-dimensional selective excitation type pulse sequence.

12. The magnetic resonance imaging apparatus according to claim 1, further comprising:
    a shim image acquisition unit that acquires a shim image of a region including the focus region; and
    a shim gradient magnetic field generation unit that corrects non-uniformity of a static magnetic field of an imaging region,
    wherein the irradiation frequency adjustment unit sets the initial irradiation frequency for the two-dimensional selective excitation magnetic field of the two-dimensional selective excitation type pulse sequence and also controls the shim gradient magnetic field generation unit to make static magnetic field distribution in the focus region uniform according to static magnetic field distribution obtained by the shim image when the two-dimensional selective excitation type pulse sequence is executed.

13. The magnetic resonance imaging apparatus according to claim 11,
wherein the irradiation frequency adjustment unit includes an adjustment unit that adjusts a gain of the two-dimensional selective excitation magnetic field and the gradient magnetic field strength after matching a resonance frequency in the focus region to the initial irradiation frequency.

14. The magnetic resonance imaging apparatus according to claim 2,
wherein the region setting section collects echo signals from a two-dimensional selection region designated by an operator according to the two-dimensional selective excitation type pulse sequence, and determines and sets the focus region on the basis of a projection image obtained by a Fourier transform of the echo signals.

15. An irradiation frequency adjusting method of adjusting an irradiation frequency of a two-dimensional selective excitation magnetic field when executing a two-dimensional selective excitation type pulse sequence in a magnetic resonance imaging apparatus, comprising:
  setting a focus region in a columnar region excited by a two-dimensional selective excitation magnetic field;
  collecting echo signals from the focus region using an initial irradiation frequency set in advance; and
  calculating an irradiation frequency from the echo signals collected from the focus region and setting the calculated irradiation frequency as a selective excitation irradiation frequency which is an irradiation frequency of the two-dimensional selective excitation magnetic field.

\* \* \* \* \*